United States Patent [19]

Ganzer et al.

[11] Patent Number: 5,424,443
[45] Date of Patent: Jun. 13, 1995

[54] SUBSTITUTED BENZOTHIAZOLE DERIVATIVES, THEIR PREPARATION AND USE AS HERBICIDES

[75] Inventors: Michael Ganzer; Gabriele Dorfmeister; Wilfried Franke; Gerhard Johann; Richard Rees, all of Berlin, Germany

[73] Assignee: Schering Aktiengesellschaft, Germany

[21] Appl. No.: 142,440
[22] PCT Filed: May 21, 1992
[86] PCT No.: PCT/EP92/01268
 § 371 Date: Jan. 24, 1994
 § 102(e) Date: Jan. 24, 1994
[87] PCT Pub. No.: WO92/20675
 PCT Pub. Date: Nov. 26, 1992

[30] Foreign Application Priority Data

May 24, 1991 [DE] Germany .................. 41 17 508.5

[51] Int. Cl.⁶ .................. C07D 417/04; A01N 43/90; A01N 43/78; A01N 43/836
[52] U.S. Cl. .................. 548/159; 548/120; 548/121; 548/128; 548/132; 548/162; 504/246; 504/262; 504/263; 504/265; 504/268
[58] Field of Search ............... 504/268, 265, 246, 262, 504/263; 548/159, 162, 132, 120, 121, 128

[56] References Cited

FOREIGN PATENT DOCUMENTS 0311135 4/1989 European Pat. Off. .
0349748 1/1990 European Pat. Off. .
0373461 6/1990 European Pat. Off. .

OTHER PUBLICATIONS

*Chem Pharm Bull*, vol. 27, No. 1, Norio Suzuki (author), pp. 1-11, Jan. 1979.
A. T. Blomquist, "Benzothiazoles. II. Nuclear Chlorination in the Herz Process", J. of Org. Chem., vol. 12, No. 5, pp. 718-725, Sep. 1947.
Chem Abstracts 48:2689A-D, Yoshihisa Mizuno, 1954.
Chem Abstracts, 54:22579d, 1960.

*Primary Examiner*—C. Warren Ivy
*Assistant Examiner*—D. Margaret M. Mach
*Attorney, Agent, or Firm*—Ostrolenk, Faber, Gerb & Soffen

[57] ABSTRACT

The invention relates to new substituted benzothiazole derivatives of general formula (I), in which X, Y and Z have the meanings given in the description, processes for their preparation and their use as herbicides.

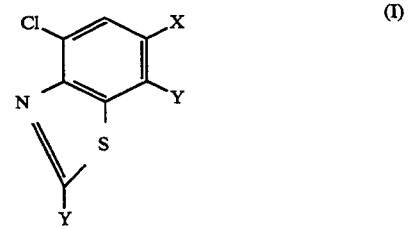

(I)

16 Claims, No Drawings

SUBSTITUTED BENZOTHIAZOLE DERIVATIVES, THEIR PREPARATION AND USE AS HERBICIDES

This is the U.S. National Phase application of PCT/EP92/01268 filed May 21, 1992.

This invention relates to new substituted benzothiazole derivatives, processes for their preparation und their use as herbicides.

It is known that certain benzofuran derivatives (EP 271 170) posses herbicidal properties. However the herbicidal activity of these known compounds is not always sufficient or selectivity problems can occur in important crops.

In EP 0 373 461 are described certain benzazoles with herbicidal activity which are substituted in the 5-position, with e.g., a 3,4,5,6-tetrahydrophthalimide moiety. The linkeage at the 7-position of the benzothiazole moiety has an unexpected effect on the activity of the compounds.

It has now been found that substituted benzothiazole derivatives of general formula I

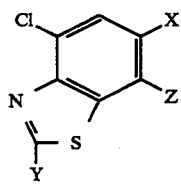
(I)

in which
X is hydrogen, fluorine or chlorine,
Y is hydrogen, fluorine, bromine, $C_1$–$C_6$-alkyl or halo-$C_1$–$C_6$-alkyl,
Z is one of the group $Z^1$ to $Z^8$ of formula

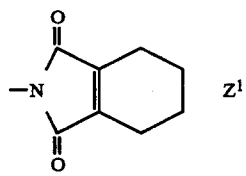 $Z^1$

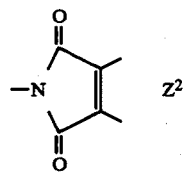 $Z^2$

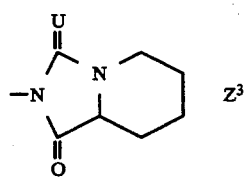 $Z^3$

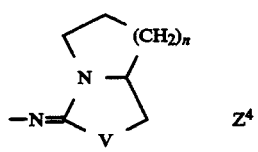 $Z^4$

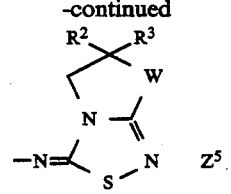 $Z^5$

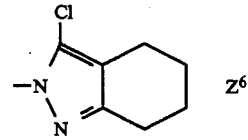 $Z^6$

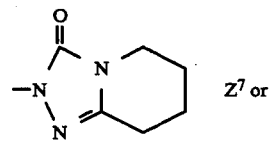 $Z^7$ or

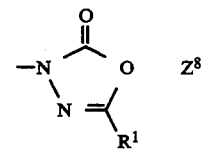 $Z^8$

U and V are oxygen or sulfur;
n is 0 or 1;
W is methylene or sulfur;
$R^1$ is $C_1$–$C_6$-alkyl; and
$R^2$ and $R^3$ are the same or different and are hydrogen or methyl;

surprisingly show an outstanding selectivity to crops whilst at the same time have interesting herbicidal activity.

The expression "halogen" means fluorine, chlorine, bromine and iodine. The term "haloalkyl" means that one or more hydrogen atoms of the alkyl group are replaced by halogen.

The compounds of general formula I can exist optionally as various enantiomers or geometric isomers and these are within the scope of the invention.

The compounds of the invention of general formula I can be prepared by a process in which
A) when Z is $Z^1$ and $Z^2$, a compound of general formula II

(II)

in which X and Y have the meanings given under general formula I, is reacted with a compound of formula III or IV

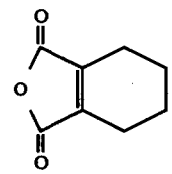
(III)

-continued or

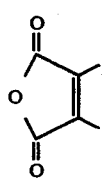
(IV)

B) when Z is $Z^3$, a compound of general formula V

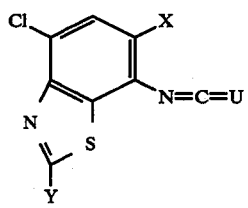
(V)

in which X, Y have the meanings given under general formula I and U is sulfur, is reacted with a compound of formula VI

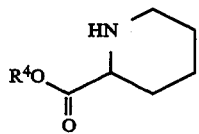
(VI)

in which in which $R^4$ is hydrogen or $C_1$–$C_4$-alkyl,

C) when Z is $Z^4$, a compound of general formula VII

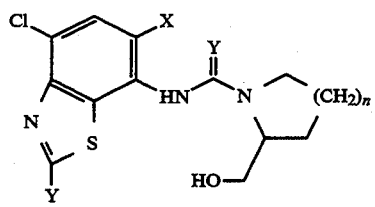
(VII)

in which X, Y and V have the meanings given under general formula I and n is 1, is cyclised.

D) when Z is $Z^5$, a compound of general formula V

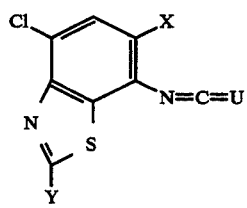
(V)

in which X and Y have the meanings given under general formula I and U is sulfur, is reacted with a compound of formula VIII

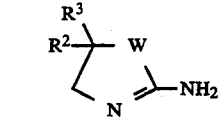
(VIII)

in which $R^2$, $R^3$ and W have the meanings given under general formula I, and the resulting compound is cyclised in the presence of an oxidising agent to the thiazole ring.

E) when Z is $Z^6$, a compound of general formula IX

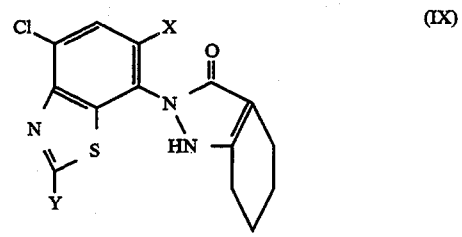
(IX)

in which X and Y have the meanings given under general formula I, is reacted with a phosphorus halide, a phosphorus oxyhalide, phosgene, thionyl chloride or oxalyl chloride, F) when Z is $Z^7$, a compound of general formula X

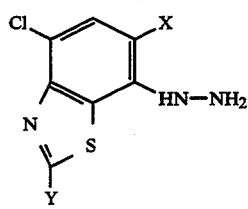
(X)

in which X and Y have the meanings given under general formula I, is reacted with a compound of formula XI

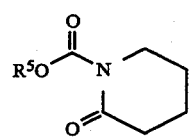
(XI)

in which $R^5$ is $C_1$–$C_4$-alkyl, in an inert solvent, in the presence of phosphorus pentoxide, or G) when Z is $Z^8$, a compound of general formula XII

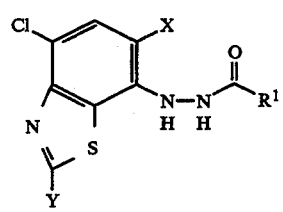
(XII)

in which $R^1$, X and Y have the meanings given under general formula I, is reacted with phosgene, thiophosgene or a functional derivative thereof.

The reaction according to process variant A) is suitably carried out by treating the starting material of general formula II in a suitable solvent with the compound of formula III or IV at a temperature between 20° and 200° C., whereby the anhydride is reacted in a molar amount of 1 to 3 equivalents to 1 equivalent of the amine of formula II. The reaction time is between 1 to 24 hours.

The reaction according to process variant A) is suitably carried out at 20° C. to 200° C., optionally in the presence of a solvent, whereby the anhydride is reacted in a molar amount of 1 to 3 equivalents to 1 equivalent of the aniline of formula II. The reaction time is between 1 to 24 hours.

Generally, the reaction is carried out in the presence of an acid, such as for example acetic acid, where the acetic acid for example can also act as solvent. It is however also possible to react both reactants using an inert solvent, such as for example toluene, with the addition of catalytic amounts of acetic acid and an organic base as dehydrating agent. Further it is possible to carry out the reaction using an inert solvent, such as for example dichloromethane or dimethyl sulfoxide and to cyclise the resulting intermediate addition products of general formula XIII or XIV

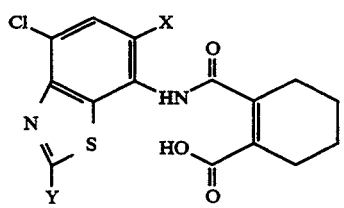

(XIII)

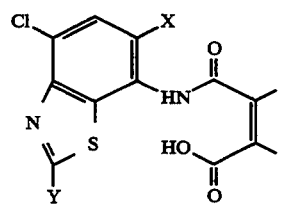

(XIV)

in which X and Y have the meanings given in general formula I with an acid anhydride, such as for example acetic anhydride.

Some of the anilines of general formula II, used as starting materials are known (Chem. Pharm. Bull. 27 (1), 1–11, (1979) (X=hydrogen) whilst others are new (X=fluorine or chlorine) and can be prepared in an analogous way to the process shown in the following reaction scheme.

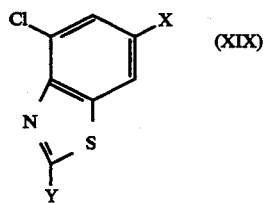

(XIX)

↓ nitration

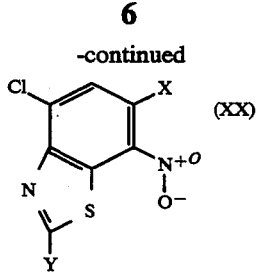

(XX)

↓ reduction

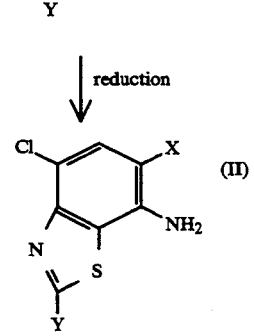

(II)

The reaction according to process variant B is suitably carried out by reacting the starting materials in an organic solvent, optionally with the addition of catalytic to equimolar amounts of an organic base, such as for example triethylamine or pyridine, over a long period, such as for example 0.5 to 15 hours, at a temperature of 20° C. up to the boiling point of the particular solvent.

Suitable solvents are those which are inert to the reaction condition such as for example toluene, acetone, acetonitrile, dimethylformamide, diethyl ether, tetrahydrofuran, dioxane, ethanol or methanol.

Optionally the uncyclised intermediate product of general formula XV

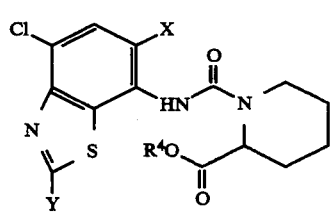

(XV)

in which $R^4$, X and Y have meanings given in general formula I can be cyclised by the addition of a mineral acid, such as for example hydrochloric acid, or by the addition of a base, such as for example sodium methanolate, and optionally by further heating up to the boiling point of the solvent.

The isocyanate and isothiocyanate of general formula V used for this reaction can be prepared in known manner processes from the anilines of general formula II.

The process variant C) is suitably carried out by reacting the urea of general formula VII, in which X and Y have the meanings given in general formula I and V is oxygen, with thionyl chloride, or the thiourea of general formula VII, in which X and Y have the meanings given in general formula I and V is sulfur, is cyclised with a strong mineral acid, such as for example hydrochloric acid, hydrobromic acid or sulfuric acid, at a temperature of 0° to 150° C. The reaction time is between 0.5 to 24 hours.

Optionally the reaction can be carried out with the addition of organic solvents, such as for example diethyl ether, tetrahydrofuran, dioxane, dichloromethane, chloroform, methanol or ethanol. After neutralising with for example caustic soda, the reaction mixture can be worked up in conventional manner.

The reaction according to process variant D can be carried out in an inert solvent, such as for example diethyl ether, methylene chloride, chloroform or ethyl acetate, at a temperature of −50° C. to +50° C., by reacting a compound of general formula V, in which X and Y have the meanings given under general formula I and U is sulfur, with a compound of general formula VIII, in which $R^2$, $R^3$ and W have the meanings given under general formula I. The reaction time is between 0.5 to 10 hours. The resulting compound of general formula XVI

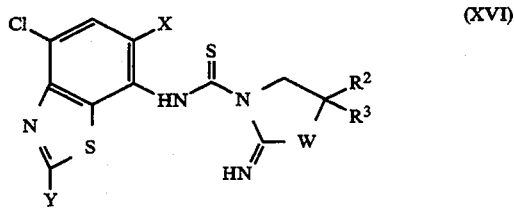

in which X, Y, $R^2$, $R^3$, and W have the meanings given under general formula I is thermally unstable and is therefore preferably reacted without isolation.

The ring formation is generally carried out using an oxidising agent in an organic solvent. Suitable inorganic solvents are inert solvents, such as for example methylene chloride, chloroform, dimethylformamide or ethyl acetate. The condensation reaction for the ring formation can be carried out in the presence of an acid acceptor usually used in conjunction with oxidising agents. Suitable acid acceptors are organic bases, such as triethylamine, pyridine, dimethylaniline, or inorganic bases, such as sodium hydroxide or sodium carbonate. Oxidising agents that can be used include bromine, chlorine or sodium hypochlorite.

The reaction according to process variant E can be optionally carried out with or without a solvent. The reaction temperature lies between room temperature and 180° C., preferably however at the reflux temperature of the reaction mixture. Suitable solvents include methylene chloride, chloroform, benzene, toluene, chlorobenzene, dichlorobenzene or xylene as well as others which are inert to the reactant.

The starting material of general formula IX used for process E can be obtained by reaction of a compound of general formula X, in which X and Y have the meanings given in general formula I with a compound of general formula XVII in which $R^6$ is $C_1$-$C_4$ alkyl, according to the following reaction scheme.

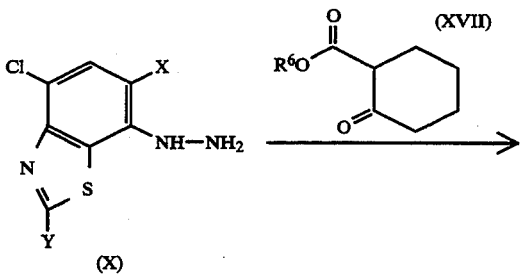

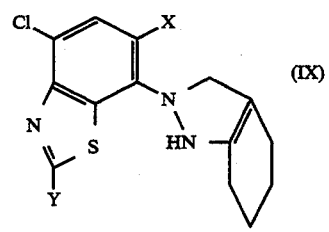

The reaction is preferably carried out in a solvent at a temperature of 80° to 200° C., over a period of 0.5 to 20 hours. Suitable solvents include ethanol, toluene, xylene or acetic acid.

The compounds of general formula IX can exist in three tautomeric forms. For simplicity, however, only the above given formula IX is shown.

The hydrazines of general formula X used as starting materials can be obtained in known manner from the anilines of general formula II, in which X and Y have the meanings given in general formula I, by treatment in an aqueous acid suspension, at a temperature of −20° to +20° C., with sodium nitrite and then reacting with a reducing agent, such as for example, tin chloride.

The process variant F is suitably carried out by reacting the starting materials of general formula X and XI in the presence of phosphorus pentoxide, in a suitable solvent at a temperature between 20° and 150° C., preferably, however, at the boiling point of the solvent. Suitable solvents include halogenated hydrocarbons, such as for example methylene chloride or chloroform, or aromatic hydrocarbons, such as for example benzene, xylene, chlorobenzene or dichlorobenzene. The reaction time is between 0.5 to 15 hours.

The reaction accordingly to process variant G can be carried out with or without the use of a suitable solvent. Suitable solvents include for example dimethyl sulfoxide, halogenated hydrocarbons, such as for example benzene, toluene, xylene, chlorobenzene and dichlorobenzene as well as other solvents which are inert to the reactants, such as for example diethyl ether, tetrahydrofuran or dimethylformamide.

The starting materials of general formula XII can be obtained by reacting a hydrazine of general formula X, in which X and Y have the means given in general formula I with an acid derivative of formula XVIII, in which $R^1$ has the meaning given in general formula I and $R^7$ is a $C_1$-$C_4$-alkoxy group or a halogen atom, according to the following reaction scheme.

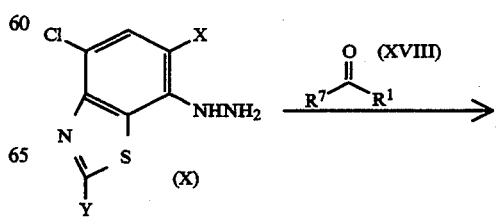

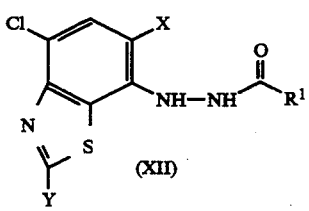

The compounds of general formula II, V, X and XX are new and form part of the invention with the proviso that in formula II and XX, X is not H.

Those starting materials whose preparation has not been described can be prepared in a similar manner to known processes.

The working up of compounds of the invention can be carried out in a conventional manner. Purification is generally carried out by recrystallisation or column chromatography.

The compounds of the invention are generally colourless to pale yellow crystalline or viscous substances, that are usually highly soluble in chlorinated hydrocarbons, such as methylene chloride or chloroform, ethers, such as diethyl ether or tetrahydrofuran, alcohols, such as methanol or ethanol, ketones such as acetone or butanone, amides such as dimethylformamide, or sulfoxides, such as dimethyl sulfoxide.

The active substances of the invention show a good herbicidal activity against broad leaved weeds and grasses. A selective use of the compounds of the invention in various crops is possible for example in rape, beet, soya beans, cotton, rice, barley, wheat and other cereals. Individual active substances are particularly suitable as selective herbicides in beet, cotton, soya and cereals. However the compounds can be used for control of weeds in permanent crops, such as for example forestry, ornamental trees, fruit, vine, citrus, nut, banana, coffee, tea, rubber, oil palm, cocoa, berry fruit and hop plantations and for the selective control of weeds in annual crops.

The compounds of the invention can used for example against the following plant species:

Dicotyledonous weeds of the species Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary, depending on the manner of pre- and postemergent use, between 0.001 and 5 kg/ha.

The compounds of the invention can also be used as defoliants, desiccants and as total herbicides.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added.

Herbicidally active mixing partners suitable in this connection include for example, the active agents listed in Weed Abstracts, vol. 39, No 1 (1990) under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitable be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulfoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulfonate, polyoxyethylenealkylphenyl ethers, naphthalenesulfonic acids and their salts, phenolsulfonic acids and their salts, formaldehyde condensates, fatty alcohol sulfates, as well as substituted benzenesulfonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

A) Wettable Powder
  1.) 20 percent by weight active ingredient
    68 percent by weight kaolin
    10 percent by weight calcium lignosulfonate 2 percent by weight dialkyl naphthalene-sulfonate
  2.) 40 percent by weight active ingredient
    25 percent by weight kaolin
    25 percent by weight colloidal silicic acid
    8 percent by weight calcium lignosulfonate
    2 percent by weight sodium salt of N-methyl-N-oleyltaurine B) Paste
  45 percent by weight active ingredient
  5 percent by weight sodium aluminium silicate
  15 percent by weight cetyl polyglycol ether with 8 tool of ethylene oxide
  2 percent by weight spindle oil
  10 percent by weight polyethylene glycol
  23 percent by weight water C) Emulsifiable Concentrate
  20 percent by weight active ingredient 75 percent by weight isophorone
2 percent by weight castor oil
3 percent by weight calcium dodecylbenzenesulfonate The following examples illustrate the preparation of compounds according to the invention.

EXAMPLE 1.01 (Process A)

N-(2,4-Dichloro-6-fluorobenzothiazol-7-yl)-3,4,5,6-tetrahydrophthalimide

A solution of 6 g 7-amino-2,4-dichloro-6-fluoro-benzothiazole and 4.3 g 3,4,5,6-tetrahydrophthalic anhydride in 50 ml acetic acid was heated under reflux for 5 hours. After cooling, the reaction solution was poured into 200 ml ice-water and the resulting crystals were separated off. They were dried at 50° C. in vacuo and then purified by column chromatography. Yield: 6.6 g=70% of theory m.p.: 139°–141° C.

In a similar manner to that described in process A, the compounds shown in the following table of general formula I were prepared.

| Example | X | Y | Z | Physic. Constant m.p.(°C.)/$n_D°$ |
|---|---|---|---|---|
| 1.02 | H | Cl | $Z^1$ | 68–69 |
| 1.03 | H | OCH$_3$ | $Z^1$ | 170–178 |
| 1.04 | F | Cl | $Z^2$ | 133–135 |
| 1.05 | Cl | Cl | $Z^1$ | 169–171 |
| 1.06 | F | Br | $Z^1$ | 137 |
| 1.07 | F | CH$_3$ | $Z^1$ | 166–168 |
| 1.08 | F | H | $Z^1$ | 174–176 |
| 1.09 | F | CF$_3$ | $Z^1$ | 145–146 |
| 1.10 | F | C$_2$H$_5$ | $Z^1$ | 143–145 |
| 1.11 | F | i-C$_3$H$_7$ | $Z^1$ | 125–127 |
| 1.12 | F | CH$_2$Cl | $Z^1$ | 151–153 |
| 1.13 | F | C$_2$F$_5$ | $Z^1$ | |
| 1.14 | F | C$_3$F$_7$ | $Z^1$ | 1.5165 (34.2°) |
| 1.15 | F | CH$_2$Br | $Z^1$ | |
| 1.16 | F | c-C$_6$H$_{11}$ | $Z^1$ | 57–59 |
| 1.17 | F | t-C$_4$H$_9$ | $Z^1$ | 126–128 |
| 1.18 | F | n-C$_4$H$_9$ | $Z^1$ | |
| 1.19 | F | i-C$_5$H$_{11}$ | $Z^1$ | |
| 1.20 | F | n-C$_6$H$_{13}$ | $Z^1$ | |

Preparation of Starting Materials 2,4-dichloro-6-fluoro-7-nitrobenzothiazole 23.7 g 2,4-Dichloro-6-fluorobenzothiazole was dissolved in 100 ml concentrated sulfuric acid and the solution cooled to 0° C. To this was added very slowly, dropwise, a cooled solution of 14 ml concentrated sulfuric acid and 14 ml 100% nitric acid. The mixture was stirred for 3 hours, poured into 500 ml ice water, the resulting crystals filtered off, washed with water until neutral and dried in vacuo. Yield: 22.7 g=79% of theory m.p.: 110°–112° C.

In a similar way, the compounds shown on the following table of general formula XX were prepared.

| X | Y | Physic. Constant m.p.(°C.) |
|---|---|---|
| Cl | Cl | 119–121 |
| F | Br | 147–149 |
| F | CH$_3$ | 140–142 |
| F | H | |

7-amino-2,4-dichloro-6-fluorobenzothiazole 5 g Iron powder was added to 40 ml 5% aqueous acetic acid. The mixture was heated to reflux and a solution of 5 g 2,4-dichloro-6-fluoro-7-nitrobenzothiazole in 40 ml acetic acid and 40 ml ethyl acetate was added. The mixture was heated for 2 hours under reflux and after cooling the mixture was filtered over celite, the phases separated and the aqueous phase extracted with ethyl acetate. The combined organic phases were washed with aqueous sodium hydrogen carbonate and water and dried with magnesium sulfate. Yield: 4.3 g=97% of theory m.p.: 173° C.

In a similar way the following compounds of general formula II were prepared.

| X | Y | Physic. Constant m.p.(°C.) |
|---|---|---|
| Cl | Cl | 194–196 |
| F | Br | 159–161 |
| F | CH$_3$ | 133–134 |
| F | H | 154–156 |
| F | CF$_3$ | 148–150 |

EXAMPLE 2.01. (Process B)

N-(2,4-dichloro-6-fluorobenzothiazol-7-yl)-perhydroimidazo[1,5-a]pyridine-1,3-dione 2.6 g Ethyl piperidine-2-carboxylate was added to a solution of 4.2 g 2,4-dichloro-6-fluoro-7-isocyanatobenzothiazole in 50 ml tetrahydrofuran. The mixture was heated for 5 hours under reflux. After cooling, the solvent was removed in vacuo and the residue recrystallised several times from ethyl acetate. Yield: 2.5 g=42% of theory m.p.: 168°–170° C.

In a similar manner the following compounds of general formula I were prepared.

| Example | X | Y | U | Physic. Constant m.p.(°C.) |
|---|---|---|---|---|
| 2.02 | F | Cl | S | 238–239 |
| 2.03 | F | H | O | 194–196 |
| 2.04 | F | C$_2$H$_5$ | O | |
| 2.05 | F | C$_2$F$_5$ | O | |
| 2.06 | F | i-C$_3$H$_7$ | O | |
| 2.07 | F | n-C$_4$H$_9$ | S | |
| 2.08 | F | t-C$_4$H$_9$ | O | |
| 2.09 | F | n-C$_6$H$_{11}$ | O | |

Preparation of starting material of formula V 2,4-Dichloro-6-fluoro-7-isocyanatobenzothiazole 31 ml of a 20% solution of phosgene in toluene was added, dropwise, at room temperature to a suspension of 5.1 g 7-amino-2,4-dichloro-6-fluorobenzothiazole hydrochloride in 30 ml abs. toluene. The mixture was heated for 8 hours at 100° C. and the toluene removed in vacuo. The residue was triturated with hexane. Yield: 4.8 g=90% of theory m.p.: 95°–98° C.

2,4-Dichloro-6-fluoro-7-isothiocyanatobenzothiazole

A suspension of 16.9 g calcium carbonate in 100 ml water was added to a solution of 19.4 g thiophosgene in 100 ml dichloromethane. A solution of 40 g 7-amino-2,4-dichloro-6-fluorobenzothiazole in 500 ml dichloromethane was added, dropwise at 5° C., and the mixture stirred for 8 hours at room temperature. The solid was filtered, the phases were separated, and the organic phase dried over magnesium sulfate and concentrated. The residue was purified by column chromatography (eluent: hexane/ethyl acetate). Yield: 16 g=38% of theory m.p.: 80°–81° C.

EXAMPLE 3.01 (Process C)

2,4-dichloro-6-fluoro-7-(perhydropyrrolo[1,2-c]thiazol-3-ylidenimino)benzothiazole 1.9 g 2,4-dichloro-6-fluoro-7-(2-hydroxymethylpyrrolidino-thiocarbonylaminobenzothiazole was allowed to stand for 12 hours at room temperature in 100 ml ethanol, saturated with hydrochloric acid gas and the mixture then heated at 60° C. for 4 hours. The ethanol was distilled off, the residue taken up in dichloromethane and shaken with sodium hydrogen carbonate, dried over magnesium sulfate and concentrated. The residue was purified by column chromatography. Yield: 0.34 g=19% of theory m.p.: 115°–116° C.

In a similar way the following compound of formula I was prepared.

| Example | X | Y | n | V | Physic. Constant m.p.(°C.) |
|---|---|---|---|---|---|
| 3.02 | F | Cl | 2 | S | 48–50 |

EXAMPLE 4.01 (Process D)

2,4-Dichloro-7-(6,6-dimethyl-3,5,6,7-tetrahydropyrrolo-[2,1-c][1,2,4]thiadiazol-3-ylidenamino)-6-fluorobenzothiazole A solution of 2 g 2,4-dichloro-6-fluoro-7-isothiocyanatobenzothiazole in 10 ml dichloromethane was added, dropwise, at 0° C., to a suspension of 1.1 g 2-amino-4,4-dimethylpyrroline hydrochloride in 20 ml dichloromethane. A solution of 0.3 g sodium hydroxide and 6 ml water was added, dropwise, at 2° C. to this mixture which was stirred for 3 hours, whereby the temperature rose to 20° C. The mixture was cooled to −10° C. and a solution of 1 g bromine in 10 ml dichloromethane was added, dropwise, slowly and the mixture stirred for 1 hour whereby the temperature rose to 10° C. The solution was washed with water and with dilute caustic soda, dried over magnesium sulfate and concentrated. The residue was recrystallised from diisopropyl ether. Yield: 1.5 g=53% of theory m.p.: 134°–136° C.

In a similar manner the following compounds of formula I were prepared.

| Example | X | Y | W | R² | R³ | Physic. Constant m.p.(°C.) |
|---|---|---|---|---|---|---|
| 4.02 | F | Cl | CH₂ | H | H | 188–190 |
| 4.03 | F | Cl | S | CH₃ | CH₃ | 158–160 |
| 4.04 | F | Cl | CH₂ | CH₃ | H | 154–156 |
| 4.05 | F | Br | CH₂ | CH₃ | CH₃ | |
| 4.06 | F | iC₃H₇ | CH₂ | CH₃ | CH₃ | |
| 4.07 | F | C₂F₅ | CH₂ | CH₃ | CH₃ | |
| 4.08 | F | H | CH₂ | CH₃ | CH₃ | |

EXAMPLE 5.01 (Process F)

3-Chloro-2-(2,4-dichloro-6-fluorobenzothiazol-7-yl)-4,5,6,7-tetrahydro-2H-indazole 0.2 g 2-(2,4-Dichloro-6-fluorobenzothiazol-7-yl)1,3,4,5,6,7-hexahydro-2H-indazol-3-one was treated with 2 ml phosphorus oxychloride and the mixture stirred for one hour under reflux. After cooling, it was poured into ice-water, extracted with ethyl acetate and the organic phase washed with sodium hydrogen carbonate and water. It was dried over magnesium sulfate and concentrated. The residue was purified by column chromatography. Yield: 0.07 g=32% of theory m.p.: 161°–163° C.

Preparation of the starting material 2,4-dichloro-6-fluoro-7-hydrazinobenzothiazole 14.7 g 7-amino-2,4-dichloro-6-fluorobenzothiazole was dissolved in 128 ml concentrated hydrochloric acid and the mixture stirred for 30 minutes at room temperature. It was then cooled to −5° C. and, very slowly, a solution of 4.5 g sodium nitrite in 9.5 ml water was added, dropwise. The mixture was stirred for one hour and cooled to −15° C. At this temperature, a solution of 31.5 g tin (II) chloride in 19 ml concentrated hydrochloric acid was added, dropwise at a rate that the temperature did not rise above −8° C. The mixture was stirred for one hour, made alkaline using caustic soda, whilst cooling, and extracted with dichloromethane. The extract was dried over magnesium sulfate and concentrated. Yield: 7.8 g=50% of theory m.p.: 162°–180° C.

2-(2,4-dichloro-6-fluorobenzothiazole-7-yl)-1,3,4,5,6,7-hexahydro-2H-indazol-3-one A solution of 3 g 2,4-dichloro-6-fluorobenzothiazole in 15 ml acetic acid was treated with 1.9 ml ethyl 2-cyclohexanonecarboxylate and the mixture heated under reflux for 2 hours. The acetic acid was removed in vacuo and the residue purified by column chromatography. Yield: 0.21 g=5% of theory m.p.: 191°–197° C.

EXAMPLE 6.01 (Process G)

3-(2,4-dichloro-6-fluorobenzothiazol-7-yl)-5-(1,1-dimethylethyl)-1,3,4-oxadiazol-2(3H)-one A solution of 1,4 g 2,4-dichloro-6-fluoro-7-[N-(2,2-dimethylpropanoyl)hydrazino]benzothiazole in 8 ml of a 20% solution of phosgene in toluene was heated for 8 hours at 100° C. After cooling, the toluene was removed in vacuo and the residue taken up in dichloromethane. The extract was shaken with aqueous sodium hydrogen carbonate and water, dried over magnesium sulfate and concentrated. The residue was recrystallised from isopropanol/diisopropyl ether. Yield: 0.5 g=40% of theory. m.p.: 157°–158° C.

The starting material was prepared as follows:

2,4-dichloro-6-fluoro-7-[N-(2,2-dimethylpropanoyl)hydrazino]benzothiazole 2.6 ml Triethylamine was added to a solution of 4.8 g 2,4-dichloro-6-fluoro-7-hydrazinobenzothiazole in 38 ml toluene. 2.4 ml Pivaloyl chloride was added dropwise and the mixture stirred for 2 hours at room temperature. It was then treated with ethyl acetate and washed with aqueous sodium hydrogen carbonate and water, dried over magnesium sulfate and concentrated. The residue was purified by column chromatography. Yield: 1.36 g=21% of theory 184°–185° C.

The following examples illustrate the possibilities for use of the compounds of the invention.

Test Example A

In a greenhouse, the noted plant species were treated post-emergently with the noted compounds of the invention, at a rate of 0.03 kg active ingredient/ha. The compounds of the invention were sprayed evenly over the plants. Two weeks after the treatment, the compounds of the invention showed high selectivity in wheat (TRZAX) and Brassica spp. (BRSSS) with excellent activity against the weeds. The comparison material did not show similar high selectivity and efficacy.

| Compound | BRSSS | TRZAX | GALAP | VERPE |
|---|---|---|---|---|
| 1.02 | — | — | 3 | — |
| 1.01 | 0 | 0 | 3 | 4 |
| 3.01 | 0 | 1 | 3 | — |
| 3.02 | 1 | 0 | 3 | — |
| 4.03 | 1 | 0 | 3 | — |
| Untreated | 0 | 0 | 0 | 0 |
| Comparison | | | | |
| Oxadiazon | 2 | 1 | 2 | 2 |

Bayer Code
BRSSS = *Brassica sp.*
TRZAX = *Triticum aestivum*
GALAP = *Galium aparine*
VERPE = *Veronica persica*

0 = no damage
1 = 1–24% damage
2 = 25–74% damage
3 = 75–89% damage
4 = 90–100% damage Test Example B In a greenhouse, the compounds in the following table were applied at the given rates. The active ingredients were pipetted onto the water surface. The test plants, which were treated pre-emergently, were ORYSA, CYPDI and MOOVA in the 1–3 leaved stage.

The compound of the invention showed strong activity against CYPDI and MOOVA (important rice weeds) with good selectivity in paddy rice.

| Compound | Water application (kg/ha) | ORYSA | CYPDI | MOOVA |
|---|---|---|---|---|
| 1.03 | 0.25 | 0 | 3 | 3 |
| 1.01 | 0.25 | 0 | 4 | 4 |
| 4.02 | 0.25 | 0 | 4 | 4 |
| 2.01 | 0.25 | 0 | 4 | 3 |
| 4.01 | 0.25 | 0 | 3 | 4 |
| 1.04 | 0.25 | 0 | 4 | 3 |
| 1.02 | 0.25 | 0 | 4 | — |
| 3.01 | 0.125 | 0 | 4 | 4 |
| 3.02 | 0.125 | 0 | 4 | 4 |
| 4.03 | 0.125 | 0 | 4 | 4 |
| Untreated | | 0 | 0 | 0 |

Bayer Code
ORYSA = *Oryza sativa*
CYPDI = *Cyperus difformis*
MOOVA = *Monochoria vaginalis*

0 = no damage
1 = slight damage
2 = medium damage
3 = heavy damage
4 = total destruction

We claim:

1. Substituted benzothiazole derivative of the formula I

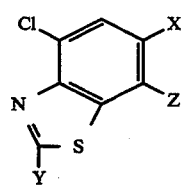

(I)

in which

X is hydrogen, fluorine or chlorine,

Y is hydrogen, fluorine, bromine, $C_1$–$C_6$-alkyl, halo-$C_1$–$C_6$-alkyl,

Z is one of the group $Z^1$ to $Z^8$ of formula

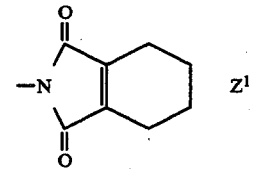

$Z^1$

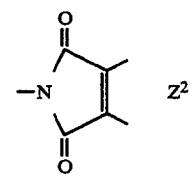

$Z^2$

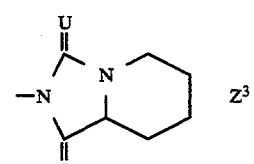

$Z^3$

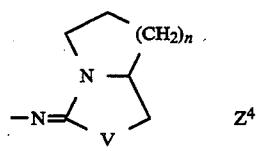

$Z^4$

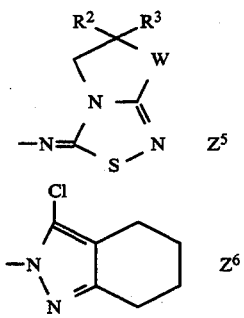

$Z^5$ $Z^6$

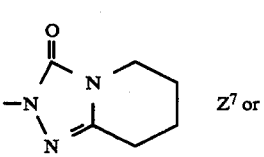

$Z^7$ or

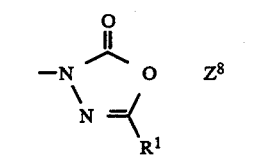

$Z^8$

U and V are oxygen or sulfur;
n is 0 or 1;
W is methylene or sulfur;
$R^1$ is $C_1$–$C_6$-alkyl; and
$R^2$ and $R^3$ are the same or different and are hydrogen or methyl.

2. Benzothiazole of the formula

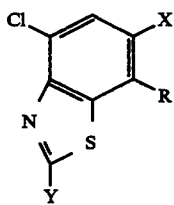

in which
R is amino, cyanato, thiocyanato, hydrazino or nitro;
X is hydrogen, fluorine or chlorine; and
Y is hydrogen, fluorine, bromine, $C_1$–$C_6$-alkyl, halo-$C_1$–$C_6$-alkyl, $C_1$–$C_6$-alkoxy or halo-$C_1$–$C_6$alkoxy, with the provisio when R is amino or nitro,
X is fluorine.

3. A herbicidal composition which comprises a compound according to claim 1, in admixture with carriers and diluents.

4. A method of combating weeds which comprises applying to the weeds or their locus a compound according to claim 1.

5. Substituted benzothiazole derivative according to claim 1 in which Z is $Z^1$, X is hydrogen, chlorine or fluorine and Y is fluorine, ethyl or methoxy.

6. Substituted benzothiazole derivative according to claim 1 in which Z is $Z^3$, U is oxygen, X is chlorine and Y is fluorine.

7. Substituted benzothiazole derivative according to claim 1 in which Z is $Z^4$, X and Y individually are fluorine or chlorine and V is sulphur.

8. Substituted benzothiazole derivative according to claim 1 in which Z is $Z^5$, $R^2$ and $R^3$ are individually hydrogen or methyl, X and Y are individually fluorine or chlorine and W is sulphur or methyl.

9. A herbicidal composition which comprises a compound according to claim 5, in admixture with carriers and diluents.

10. A herbicidal composition which comprises a compound according to claim 6, in admixture with carriers and diluents.

11. A herbicidal composition which comprises a compound according to claim 7, in admixture with carriers and diluents.

12. A herbicidal composition which comprises a compound according to claim 8, in admixture with carriers and diluents.

13. A method of combating weeds which comprises applying to the weeds or their locus a compound according to claim 5.

14. A method of combating weeds which comprises applying to the weeds or their locus a compound according to claim 6.

15. A method of combating weeds which comprises applying to the weeds or their locus a compound according to claim 7.

16. A method of combating weeds which comprises applying to the weeds or their locus a compound according to claim 8.

* * * * *